United States Patent

Gieloff et al.

[11] Patent Number: 5,562,450
[45] Date of Patent: Oct. 8, 1996

[54] PROCESS FOR THE PRODUCTION OF A DENTAL IMPLANT

[75] Inventors: Burkhardt Gieloff, Denzlingen; Gerold Klaus, Kenzingen; Bernd Rademacher, Hagen; Wolfgang Dörken, Hilzingen, all of Germany

[73] Assignee: Reimplant Dentale Systeme GmbH, Hagen, Germany

[21] Appl. No.: 422,324

[22] Filed: Apr. 13, 1995

[30] Foreign Application Priority Data

Jul. 19, 1994 [DE] Germany ............... 44 25 425.3

[51] Int. Cl.⁶ ................ A61C 5/10; A61C 8/00
[52] U.S. Cl. .................. 433/223; 433/201.1
[58] Field of Search .................. 433/68, 172, 173, 433/174, 175, 176, 201.1, 223

[56] References Cited

U.S. PATENT DOCUMENTS

| | | | |
|---|---|---|---|
| 4,615,678 | 10/1986 | Moermann et al. | 433/201.1 |
| 4,837,732 | 6/1989 | Brandestini et al. | 433/223 X |
| 5,004,422 | 4/1991 | Propper | 433/201.1 X |
| 5,266,030 | 11/1993 | Van Der Zel | 433/223 X |
| 5,320,462 | 6/1994 | Johansson et al. | 433/223 X |
| 5,401,170 | 3/1995 | Nonomura | 433/223 X |

Primary Examiner—Nicholas D. Lucchesi

[57] ABSTRACT

In a process for the production of a dental implant wherein the tooth root region of a natural tooth, which region has been removed from a tooth socket or the like cavity in the jaw, is copied or modelled on an implant blank comprising a biologically compatible, non-resorbable material, wherein the modelling operation is effected in particular by copy-milling, the cross-sectional dimensions of the tooth root of the natural tooth are extended in predetermined zones by double a gap dimension. In addition the basic anatomical shape of the implant is produced by contact-less sensing of the tooth root of the natural tooth by a laser beam or sonography and the gap dimensions are added as calculation values.

9 Claims, 1 Drawing Sheet

PROCESS FOR THE PRODUCTION OF A DENTAL IMPLANT

BACKGROUND OF THE INVENTION

The invention concerns a process for the production of a dental implant, wherein the tooth root region of a natural tooth, which region has been removed from a tooth socket or the like cavity in the jaw, is copied or modelled on an implant blank comprising a biologically compatible, non-resorbable material, wherein the modelling operation is effected in particular by copy-milling.

The most widely varying forms of industrially produced implants are known in implantology.

In order to place such cylindrical, screw or sheet implants in the jaw, dimensionally accurate artificial root sockets or cavities must be milled into the jaw, using milling cutters which are congruent in respect of shape. The success of that operation depends directly on the osseous healing of the implants in position, so-called genuine osseointegration. That can occur only if there is a gap-free contact between the jawbone and the implant. If that is not the case connective tissue grows into that gap and, like an insulating layer, prevents the osseous jaw/implant connection from being made.

When a tooth is drawn from a patient, it is possible for a ready-made implant to be fitted as an mediate implant into the tooth socket from which the tooth has been removed and which is now empty, in the hope that the new implant will grow fixed therein.

German laid-open application (DE-OS) No 27 29 969 describes the insertion of an implant which is substantially modelled on or is a copy of the removed tooth. It can be seen from the journal "Dental-Labor" (XXXVIII, issue 11/90), that such a configuration of a blank can be produced—for example from titanium—by a procedure involving copy-milling.

In the process for modelling or copying the root of the removed tooth by means of copy-milling from metal or ceramic material and using it as an immediate implant, it has been found that, before implantation into a natural tooth socket, the connective tissue which naturally occurs there has to be removed by being scraped out or curetted. As a result of that measure and mechanical enlargement of the tooth socket in the extraction procedure, the original tooth socket is changed in such a way that it is not possible to produce a usable implant by means of a copy of the extracted tooth.

SUMMARY OF THE INVENTION

Ideally, the implant should bear against the individual bone layers with differentiated compression pressure, and for that reason the inventor set himself the aim of providing for suitable adaptation of an implant to the parameters of the cavity, this also in relation to copy-milled implants.

That object is attained by the teaching of the independent claim while the appendant claims set forth further configurations.

In accordance with the invention the difference between the original configuration of the tooth socket on the one hand and the contour after the extraction procedure on the other hand is so compensated that gap-free contact and thus genuine osseointegration between the jawbone and the implant is possible. The cross-sectional dimensions of the tooth root of the natural tooth are extended in predetermined zones by double the gap dimension.

In accordance with a further feature of the invention the basic anatomical form of the individual implant is produced by contact-less sensing of the root of the natural tooth—possibly also a molding or casting of the tooth socket—by means of a laser beam or sonography, and the gap dimensions are added as calculation values.

Accordingly the definitive form of the implant is provided by computer simulation, with consideration being given to altered anatomical parameters; it has proven to be desirable that the deliberate and specific simulative dimensional variation in respect of the natural tooth root permits controlled osseointegration.

Even if copy-milling is preferred, the described operating procedure can also be used in relation to erosion processes or water-jet cutting.

DESCRIPTION OF THE DRAWING

Further advantages, features and details of the invention are apparent from the following description of a preferred embodiment and with reference to the diagramatically simplified views in the drawing in which.

DESCRIPTION OF SPECIFIC EMBODIMENT

Figure 2:
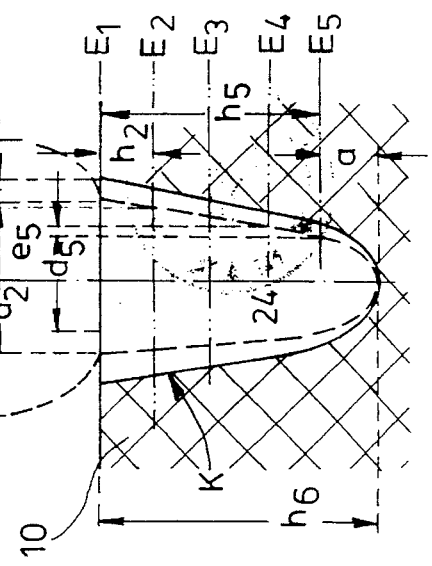
FIG. 2 is a detail on an enlarged scale from FIG. 1.

From an alveolar process 10 of a human upper or lower jaw, tooth crowns 12 of teeth which are indicated at 14 project freely into a mouth cavity from the gums (not shown in the drawing). The one-piece tooth roots 16 of the teeth 14 are each disposed in an alveolar cavity or a tooth socket 18 of the alveolar process 10.

A root or bone layer 20 which encloses the cement of the tooth root 16 and lines the inside surface of the osseous tooth socket 18 forms a unitary fiber layer which connects the natural tooth root 16 and the wall surface of the tooth socket 18. The layer 20 is extended—in a manner not shown in the drawing—outside the tooth socket 18 as gum which covers over the jaw edges.

Figure 1:
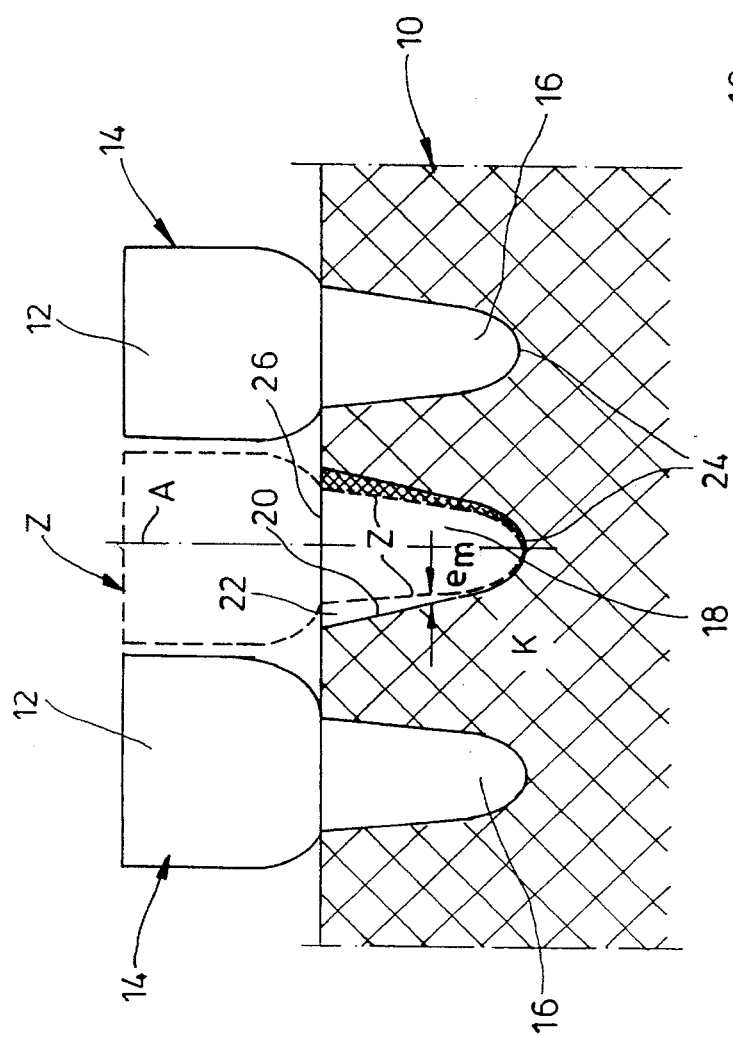
FIG. 1 is a view in cross-section through the alveolar process of a human upper or lower jaw.

The middle tooth which is indicated by a broken-line tooth contour Z in FIG. 1 has been removed by extraction; the tooth socket 18 of the depth $h_6$ has been enlarged inter alia by mechanical forces which occur in that procedure. That enlargement can be seen in the illustrated cross-sectional view between the broken-line tooth contour Z and the tooth socket contour K, in the form of the cross-sectional gap 22. Almost no dilation occurs at the cavity bottom 25, but above it the cross-sectional gap 22 of mean width $e_m$—enlarges towards the mouth opening 26 of the cavity; that is emphasized by hatching for the sake of enhanced clarity in FIG. 1 on the right beside the axis A of the tooth socket.

FIG. 2 is intended to clearly illustrate that by way of example in five zones or horizons or radial planes $E_1$ through $E_5$ through the tooth socket axis A, the planes being at the same or definedly different spacings a from each other. For example the radial plane $E_2$ is at a spacing $h_2$ relative to the cavity mouth opening 26; therein, a gap width $e_2$ is associated with the root diameter $d_2$, on both sides. In a corresponding fashion, the smaller root diameter $d_5$ in the radial plane $E_5$ is accompanied by a narrower gap width $e_5$ as the difference between the contours K and Z at that location.

The cross-sectional diameters $d_1$, $d_3$, $d_4$ are not shown in the drawing, and likewise for the gap widths $e_1$, $e_3$, $e_4$ and the heights $h_1$, $h_3$, $h_4$; those parameters can be readily seen from FIG. 2.

The contour dimensions which are taken from the tooth root 18 of the extracted tooth 14 result in the copy-milling operation in a dimensional table of approximately the following kind for diameter correction in respect of each half of the axis from the cavity mouth opening 26 in mm:

1. To length $h_2$ correction by $e_1$;
2. To length $h_3$ correction by $e_2$;
3. To length $h_4$ correction by $e_3$;
4. To length $h_5$ correction by $e_4$;
5. To length $h_6$ correction by $e_5$.

Those data inter alia serve as a design basis for the production of the individual implant; by virtue of the correction values, a correspondingly enlarged tooth root contour K is determined as the shaping travel; the anatomical information is processed individually, and both modified cavities and also the different bone substances in terms of their compressibility and pressure-carrying capability in the jaw are taken into consideration.

To determine the basic shape of the individual implant, the surface of the tooth root 16—or a mold or casting of the tooth socket 18—is defined, preferably in a contact-less mode of operation, by means of the laser reflection process or by means of sonography. Those data are stored in the computer and serve to design the basic shape.

The further data which are necessary for complete design of the individual implant are statically ascertained by evaluation of X-rays by computer tomography or possibly in dependence on the cavity depth $h_6$. The result is the above-mentioned widths $e_1$ through $e_5$ of the cross-sectional gap between the tooth root 16 and the tooth socket 18 in the various regions or zones $E_1$ through $E_5$, having regard to the removed connective tissue.

Those values are added to the ascertained tooth root surface. In addition the histological configuration of the compact and the spongy bone substance is ascertained.

The application of force involved in the chewing pressure by way of the implant should be less in the region of the compact bone substance than in the region of the spongy bone substance—which is mesh-like in terms of cross-section. Therefore the individual diameter correction for the implant must be matched to the boundary configuration of the bone tissue.

After those values have been ascertained the stored data in respect of the basic shape of the natural tooth root 16 are corrected and the new shape is calculated.

Transformation of the ideal shape of the individual implant, which is ascertained in that way, is now effected by means of a computer-controlled milling tool, or alternatively by an erosion process or by water-jet cutting.

We claim:

1. A process for the production of a dental implant, wherein the tooth root region of a natural tooth, which region has been removed from a tooth socket in a jaw, is modelled on an implant blank to form an implant, comprising a biologically compatible, non-resorbable material, the modelling operation comprising copy-milling, the improvement comprising the step of extending on the implant the cross sectional dimensions corresponding of the tooth root of the natural tooth in predetermined zones by double a gap dimension.

2. The process of claim 1 including the step of producing the basic anatomical shape of the implant by contactless sensing of the tooth of the natural tooth by a laser beam and adding the gap dimensions as calculation values.

3. The process of claim 2 including the step of producing the shape of the implant by erosion.

4. The process of claim 2 including the step of producing the shape of the implant by water-jet cutting.

5. The process of claim 1 including the step of producing the basic anatomical shape of the implant by contactless sensing of the natural tooth by sonography and adding the gap dimensions as calculation values.

6. The process of claim 5 including the step of producing the shape of the implant by erosion.

7. The process of claim 5 including the step of producing the shape of the implant by water-jet cutting.

8. The process of claim 1 including the step of producing the shape of the implant by erosion.

9. The process of claim 1 including the step of producing the shape of the implant by water-jet cutting.

* * * * *

UNITED STATES PATENT AND TRADEMARK OFFICE
CERTIFICATE OF CORRECTION

PATENT NO. : 5,562,450
DATED : October 8, 1996
INVENTOR(S) : Burkhardt Gieloff et al It is certified that error appears in the above-indentified patent and that said Letters Patent is hereby corrected as shown below:

Col. 4, line 20 change "of" to --to--.

Signed and Sealed this

Seventeenth Day of December, 1996

Attest:

BRUCE LEHMAN

Attesting Officer        Commissioner of Patents and Trademarks